US00PP22410P2

(12) United States Plant Patent
Tucker et al.

(10) Patent No.: US PP22,410 P2
(45) Date of Patent: Dec. 27, 2011

(54) ***IMPATIENS* PLANT NAMED 'TUCKMAS'**

(50) Latin Name: *Impatiens walleriana*
Varietal Denomination: TUCKMAS

(76) Inventors: James Tucker, Burton-on-Trent (GB); Jennifer Tucker, Burton-on-Trent (GB)

( * ) Notice: Subject to any disclaimer, the term of this patent is extended or adjusted under 35 U.S.C. 154(b) by 0 days.

(21) Appl. No.: 12/928,670

(22) Filed: Dec. 16, 2010

(51) Int. Cl.
*A01H 5/00* (2006.01)

(52) U.S. Cl. ..... Plt./317
(58) Field of Classification Search ..... Plt./317
See application file for complete search history.

*Primary Examiner* — Kent L Bell
(74) *Attorney, Agent, or Firm* — Penny J. Aguirre

(57) ABSTRACT

A new cultivar of *Impatiens walleriana,* 'TUCKMAS', characterized by its foliage that is variegated with green centers and greenish-white to white margins and occasional solid gold leaves during mid summer, its scarlet red flowers, its ability to be readily propagated by stem cuttings, and its similar vigor to vegetatively propagated non-variegated cultivars of *Impatiens* known to the Inventors and seed raised *Impatiens* known to the inventors.

3 Drawing Sheets

Botanical classification: *Impatiens walleriana.*
Cultivar designation: 'TUCKMAS'.

BACKGROUND OF THE INVENTION

The present invention relates to a new and distinct cultivar of *Impatiens* plant, botanically known as *Impatiens walleriana* 'TUCKMAS' and will be referred to hereafter by its cultivar name, 'TUCKMAS'.

The Inventors discovered the new cultivar, 'TUCKMAS', during production of seed raised *Impatiens* in their nursery in Burton-on Trent, Straffordshire, United Kingdom in February 2006. 'TUCKMAS' was discovered as a whole plant mutation as a single seedling from seed grown of the seed strain *Impatiens walleriana* 'F1 TEMPO' (not patented).

Asexual reproduction of the new cultivar was first accomplished by stem cuttings under the direction of the Inventors in Knutsford, Cheshire, United Kingdom. Propagation has determined that the characteristics of this cultivar are stable and are reproduced true to type in successive generations.

SUMMARY OF THE INVENTION

The following traits have been repeatedly observed and represent the characteristics of 'TUCKMAS'. These attributes in combination distinguish 'TUCKMAS' as a new and distinct cultivar of *Impatiens.*

1. 'TUCKMAS' exhibits foliage that is variegated with green centers and greenish-white to white margins.
2. 'TUCKMAS' exhibits similar vigor to vegetatively propagated non-variegated cultivars of *Impatiens* known to the Inventors and seed raised *Impatiens.*
3. 'TUCKMAS' exhibits occasional solid gold leaves during mid summer.
4. 'TUCKMAS' exhibits scarlet red flowers.
5. 'TUCKMAS' is readily propagated by stem cuttings.

The new cultivar, 'TUCKMAS', differs from its parental seed strain in having variegated foliage, whereas the foliage of the parental strain is solid green. 'TUCKMAS' is unique from other variegated forms of *Impatiens* known to the Inventors in its ease and vigor during vegetative propagation. There are also no known variegated cultivars of *Impatiens* reproduced by seed known to the Inventors at the time of this application. 'TUCKMAS' can be compared to 'Fiesta Ole Peppermint' (not patented), which differs from 'TUCKMAS' in having foliage with a thin white margin and in having double flowers that are pink and white bi-color in color. 'TUCKMAS' can also be compared to 'Variegata' (not patented), which differs from 'TUCKMAS' in having grey-green leaves with a thin white margin, in being taller in height with a more open plant habit, and in having bright pink flowers.

BRIEF DESCRIPTION OF THE DRAWING

The accompanying colored photographs illustrate the overall appearance and distinct characteristics of the new *Impatiens.* The photographs were taken of six month-old plants of 'TUCKMAS' as grown in a 12-plant hanging module in the United Kingdom.

The photograph in FIG. 1 provides an overall image of 'TUCKMAS' in bloom.

Figure 1:
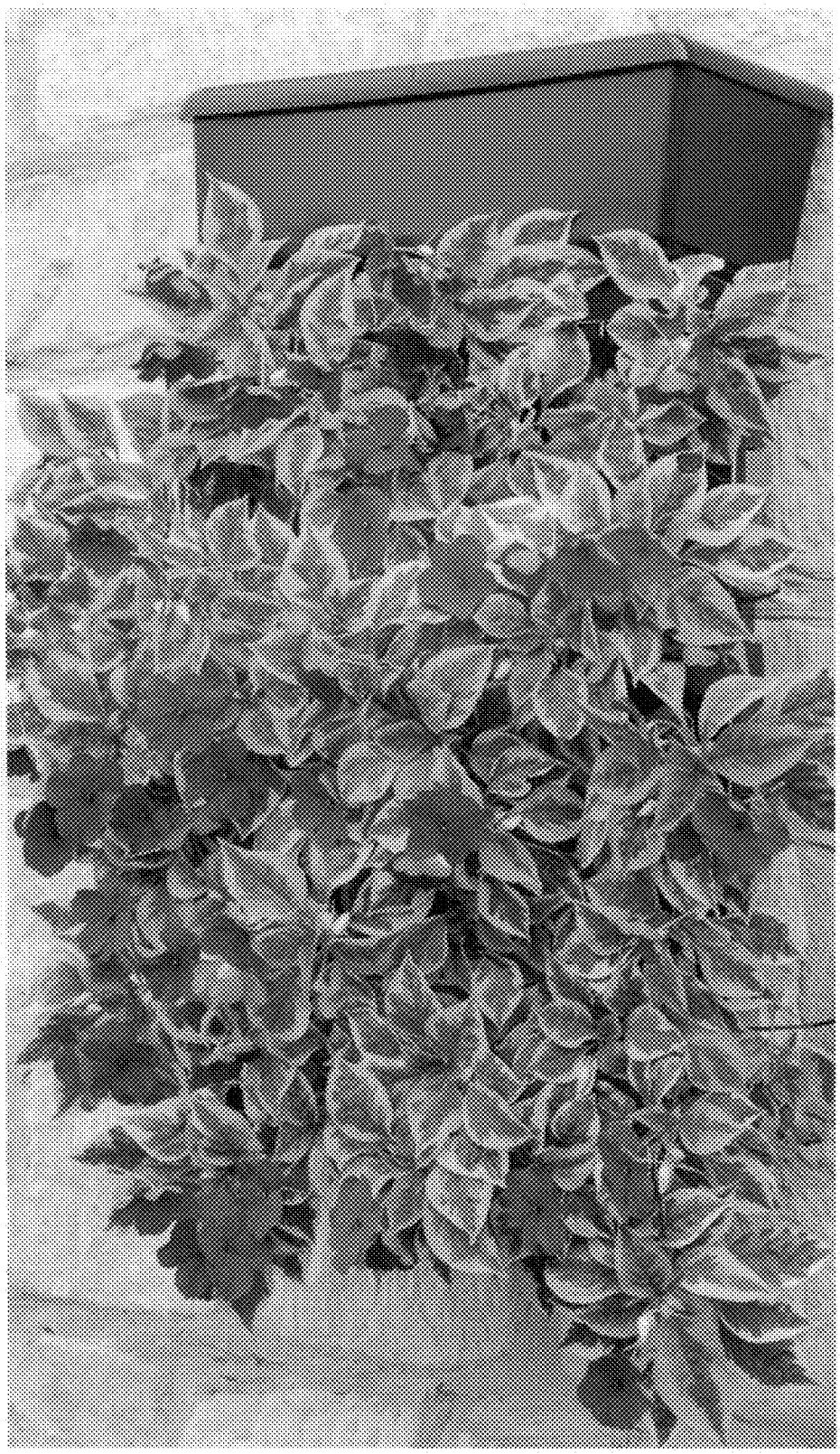
Figure 2:
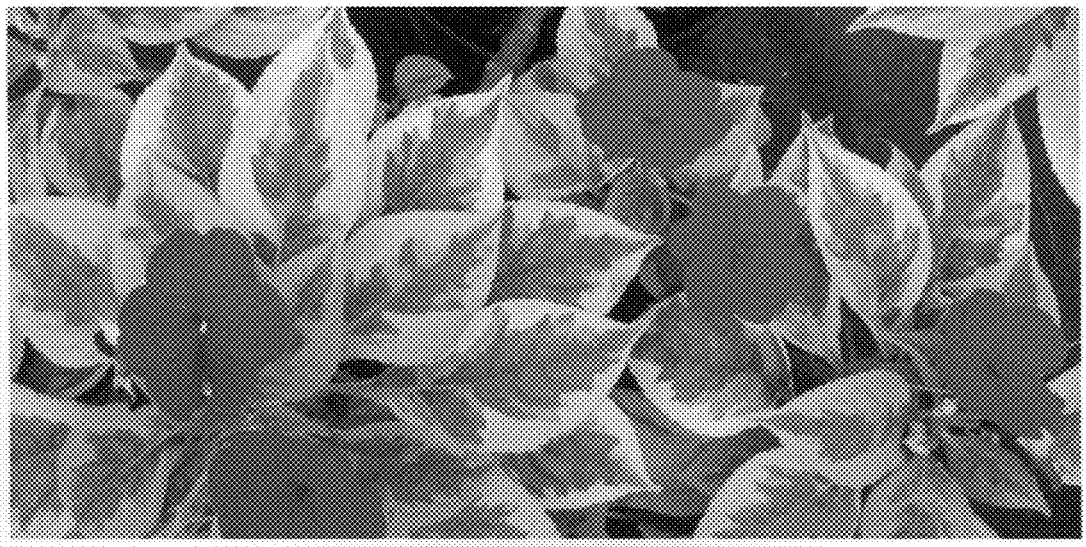

The photograph in FIG. 2 provides a close-up view of the flowers of 'TUCKMAS'.

Figure 3:
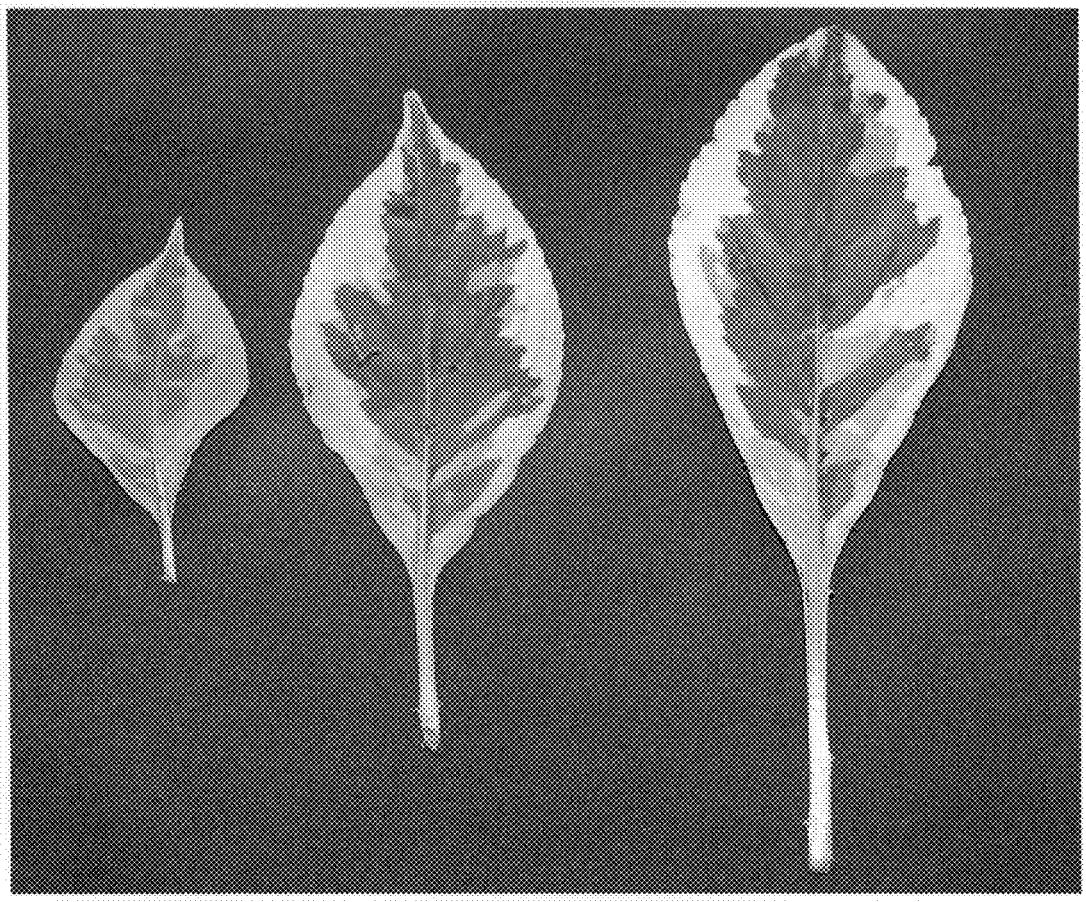

The photograph in FIG. 3 provides a view of the foliage of 'TUCKMAS' with a newly emerged leaf on the left, a maturing leaf in the center, and a fully mature leaf on the right.

Figure 4:
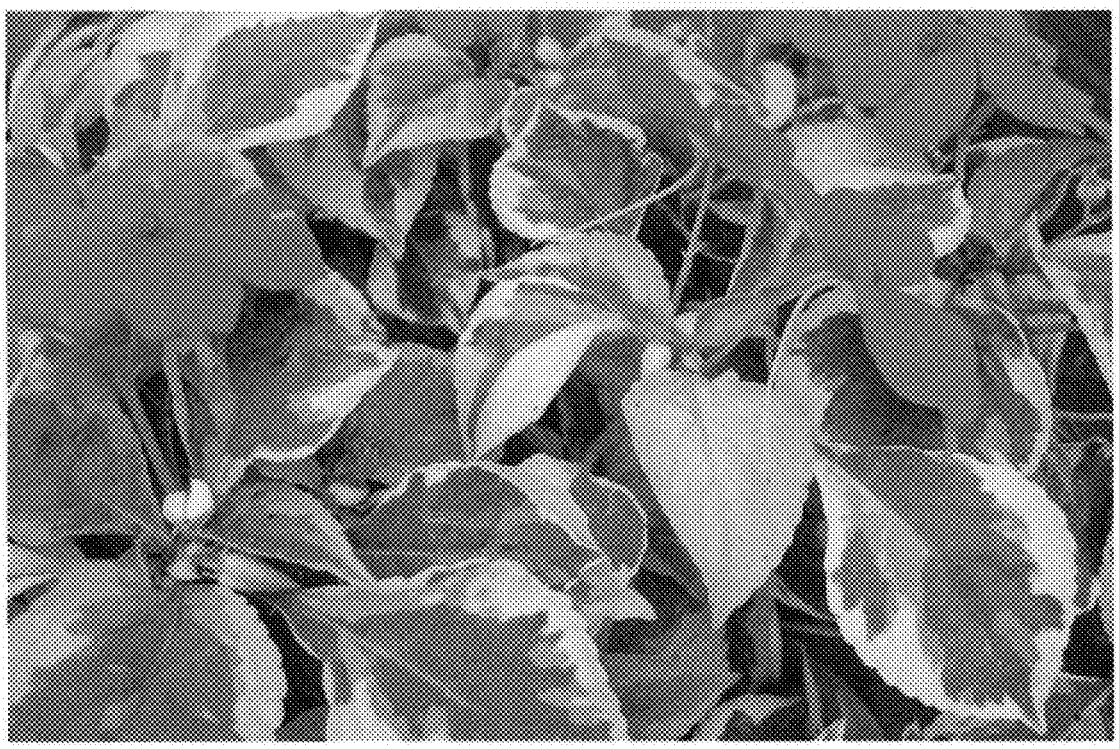

The photograph is FIG. 4 provides a view of the occasional, non-variegated golden colored leaves that are present in mid season. The colors in the photographs are as close as possible with the digital photography techniques available, the color values cited in the detailed botanical description accurately describe the colors of the new *Impatiens.*

DETAILED BOTANICAL DESCRIPTION OF THE PLANT

The following is a detailed description of 6 month-old, greenhouse grown plants of the new cultivar as grown in 3-liter containers and hanging modules in Liss, Hampshire, and Banbury, Oxfordshire United Kingdom. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

Botanical classification: 'TUCKMAS' is a cultivar of *Impatiens walleriana*.

General characteristics:

*Blooming period.*—Continuous through the growing season until November in the United Kingdom.

*Plant habit.*—Herbaceous annual with spreading growth habit.

*Height and spread.*—Reaches about 19 cm in height and about 50 cm in spread.

*Cold hardiness.*—U.S.D.A. Zone 10.

*Diseases and pests.*—Has been observed to be tolerant to mildew in Europe.

*Root description.*—Fibrous roots.

*Branching habit.*—Freely branched, lateral branches forming at about 80° from main stem.

Stem description:

*Stem.*—Round to slightly angular with age, 25 cm in length and 5 mm in width, 145B in color, surface glabrous.

*Internode length.*—5 to 8 mm in middle of stem.

Foliage description:

*Leaf shape.*—Broadly elliptic.

*Leaf division.*—Simple.

*Leaf base.*—Cuneate.

*Leaf apex.*—Acuminate.

*Leaf venation.*—Pinnate, 138A in color on upper surface and 143A on lower surface.

*Leaf margins.*—Crenate with bristles between teeth.

*Leaf attachment.*—Petiolate.

*Leaf arrangement.*—Alternate.

*Leaf surface.*—Glabrous.

*Leaf color.*—Young upper surface: center 143A and margin 144B; young lower surface: center 143D and margin 145C; maturing upper surface: center 137B with patches 188B and margin 1B; maturing lower surface: center 143D and margin 150C; mature upper surface: center 189A with patches 188B and margin 8D; mature lower surface: center 137C and margin 154D; in mid season occasional leaves occur that are 154C in color and non-variegated.

*Leaf size.*—Average of 9.5 cm in length and 5.0 cm in width.

*Leaf quantity.*—Average of 26 per lateral branch.

*Petiole.*—3.5 to 4.0 cm in length and 3 mm in width, base and lower surface 145D in color, distal end 146D in color, 1 to 3 nectariferous glands.

Flower description:

*Inflorescence type.*—Single, rotate.

*Lastingness of flowers.*—About 7 days, self cleaning.

*Flower size.*—Average of <1 mm in length excluding spur and 4.1 cm in diameter.

*Flower fragrance.*—None.

*Flower arrangement.*—2 flowers per peduncle produced in leaf axils.

*Flower number.*—Average of 2 per branch.

*Flower aspect.*—Upwards or outward.

*Flower bud size.*—Average of 1.2 mm in length, up to 9.0 mm in width.

*Flower bud color.*—Upper side 157D and 143C, lower side 157D and 186D.

*Flower bud shape.*—Broadly ovate, asymmetrically flattened.

*Petal number.*—5, unfused.

*Petal shape.*—Rounded, trimorphic.

*Petal color.*—Mature upper surface; 43A; mature lower surface 41C; larger petal upper surface distinct, 41C in color, with central stripe 144D and lateral margins 155C.

*Petal surface.*—Glabrous, slightly waxy.

*Petal margin.*—Entire.

*Petal size.*—2 small petals 2 cm in length and 1.9 cm in width, 2 medium petals 2.4 cm in length and 1.8 cm in width, 1 large petal 2.8 cm in length and 1.7 cm in width.

*Sepal number.*—3; 2 small lateral and 1 large extended into a long spur.

*Sepal shape.*—Lateral sepals linear, lower sepal ovate extending into a long spur.

*Sepal margin.*—Entire.

*Sepal size.*—Lateral sepals 2 mm in length and 0.5 mm in width; lower sepal base 1.4 cm in length and 1.1 cm in width extending into a long spur 3.5 cm in length and 1 mm in width.

*Sepal surface.*—Glabrous.

*Sepal apex.*—Acute.

*Sepal base.*—Lateral sepals cuneate, spurred sepal truncate to spur.

*Sepal color.*—Lateral sepals 144B; spurred sepal; 155D blended with 185B towards base, spur 181D in color.

*Peduncle.*—Round, 2.5 to 3.5 cm in length and 2 mm in diameter.

*Peduncle color.*—144D.

*Pedicel.*—Round, 1.7 cm in length and 1 mm in width, 144C to 144D in color.

*Bracteole.*—4, linear in shape, 3 mm in length, 0.5 mm in width, 144B to 144C in color, glabrous.

Reproductive organs:

*Gynoecium.*—1 pistil, 5 lobed stigma <1 mm in length, 144B in color, style absent, superior ovary ovoid in shape, 2 mm in length and 1 mm in width, 144B in color.

*Androcoecium.*—5 stamens; anthers fused forming a cap over gynoecium, 1 mm in length and 1.5 mm in width; filaments minute, 77A in color; pollen abundant, N74A in color.

*Fruit/seeds.*—Capsule, 5 locules, dehiscent, seeds harvested and planted at the time of this application have not produced any seedlings with variegated leaves.

It is claimed:

1. A new and distinct cultivar of *Impatiens* plant named 'TUCKMAS' as herein illustrated and described.

* * * * *